United States Patent [19]

Moore

[11] Plant 5,117

[45] Oct. 11, 1983

[54] ROSE PLANT

[75] Inventor: Ralph S. Moore, Visalia, Calif.

[73] Assignee: Sequoia Nursery, Visalia, Calif.

[21] Appl. No.: 344,031

[22] Filed: Jan. 29, 1982

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

This invention relates to a new and distinct variety of miniature rose plant primarily identified by its variegated (striped) buds and flowers of pink and white.

1 Drawing Figure

1

The present invention relates to a new and distinct variety of hardy, dwarf, bush type rose plant of the miniature class; the variety being primarily characterized — as to novelty — by the pink and white striped flowers which generally hold colors extremely well.

The variety is further characterized by:

An abundance of bloom, with flowers usually borne singly, but also several to the stem in small cluster.

Quite fragrant.

A plant which is moderately vigorous, of rounded to spreading shape with small semi-glossy to matt foliage with pointed leaflets; the buds and flowers being similar in form to Beauty Secret (miniature — not patented) but smaller in size and more double (more petals).

The plant, which has a normal height of 8–10 inches (or more) can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Darling (U.S. Plant Pat. No. 1,581, expired — floribunda) as the seed parent and an un-named seedling (miniature) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety identification.*—MORdeb (Commercial synonym: Joan Austin).

Flowers borne: Singly and several together (3 to 5) on slender wirey stems.

Quantity of bloom: Abundant both outside and in greenhouse.

Bud:

2

*Peduncle.*—Medium to short length; slender but sturdy; erect; medium green, sometimes tinted bronze (outdoors); with no prickles and few or no fuzz-like hairs.

*Before calyx breaks.*—Size — small. Form long, ovoid to pointed, with few or no foliaceous appendages on surface of bud; with foliaceous parts extending beyond the tip of the bud equal to one-half or more of its length. Color — medium green, occasionally tinted with bronze (outdoors).

*As calyx breaks.*—Color — white or pink (or both). Opening: opens well in all weather.

Bloom:

*Size when fully open.*—Small, averaging about 30–35 mm ($1\frac{1}{4}''$). Petalage — double — averaging about 35–40 (or more) petals, arranged regularly plus several small petaloids. Form — cupped at first becoming rounded with petals rolled slightly outward and downward. Open flowers usually have no stamens.

Petals: Fairly thick; satiny on inside and on outside surface.

*Shape.*—Outside petals, broad lanceolate with short acute tip; intermediate — broad lanceolate with short acute tip; inside — lanceolate with acute tip.

Color: Newly opened flower from a plant grown in plastic greenhouse (November 1981), Visalia, Calif.:

*Outside petal.*—Outside surface — white or near white and striped with pink of a shade near Rose Madder 23/2 (or lighter) and overlaid or lightly veined with darker pink, becoming white or yellowish at base. Inside surface — similar color pattern to outside surface with the pink areas being near Tyrian Rose 24/1 at deepest coloring to near Tyrian Rose 24/3 ( or lighter) with shading or veining similar to that on reverse side.

*Intermediate petal.*—Outside surface similar to outside petal. Inside surface similar to outside petal.

*Inner petal.*—Outside surface — similar to intermediate petal; inside surface — similar to intermediate petal. NOTE: The pink color can vary, depending upon weather (light intensity and temperature), from above pink shades to corresponding shades of Tyrian Rose to Fuchsine pink. General color effect; buds and newly opened flowers — white and pink stripes (or variegation) with no two petals alike. Three days open — color — similar to fresh open flowers, but less bright. Behavior — opens well in all weather. Spent petals or flowers drop off. Flower longevity (July–August 1981) — plant in pot 6–10 days or longer. Cut flowers at living room temperature 5–7 days or longer.

Reproductive organs:

*Stamens.*—Few — usually none.

*Filaments.*—Varying length (if present).

*Anthers.*—Usually none.

*Pollen.*—None.

*Pistils.*—Average number but usually not perfectly formed.

*Styles.*—Not perfectly formed, green, bunched.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; medium small; leathery; semi-glossy to matt.

*Leaflets.*—Shape; broad lanceolate, apex acute; base — acute — sometimes rounded. Color: medium green, new growth — normal (medium) green (sometimes tinted reddish). Rachis: medium strength; upper side may have a few short hairs; grooved; underside may have several small thorns (or claws) and few or no tiny prickles. Stipules: relatively long; very narrow; medium to short length narrow points which turn out at more (sometimes less ) than 45 degrees.

Growth:

*Habit.*—Dwarf; bushy; rounded; much branched.

*Growth.*—Moderately vigorous, internodes short.

*Canes.*—Medium; slender; sturdy.

*Main stems.*—Color: medium green.

*Thorns.*—Relatively few of varying size and length. Hairs — few or none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers variegated or striped (in differing degrees and patterns) with pink and white, the bud being pointed in the early opening stage, resembling in form Beauty Secret (miniature — not patented), with the open flower being rounded and full with many (35 or more) petals; and further characterized by a plant of compact, vigorous, well rounded shape; with main stems and shoots of less than average thorniness, the said plant being easy to propagate from softwood cuttings, with an abundance of small semi-glossy to matt foliage, the flowers being born singly or several to the stem in clusters.

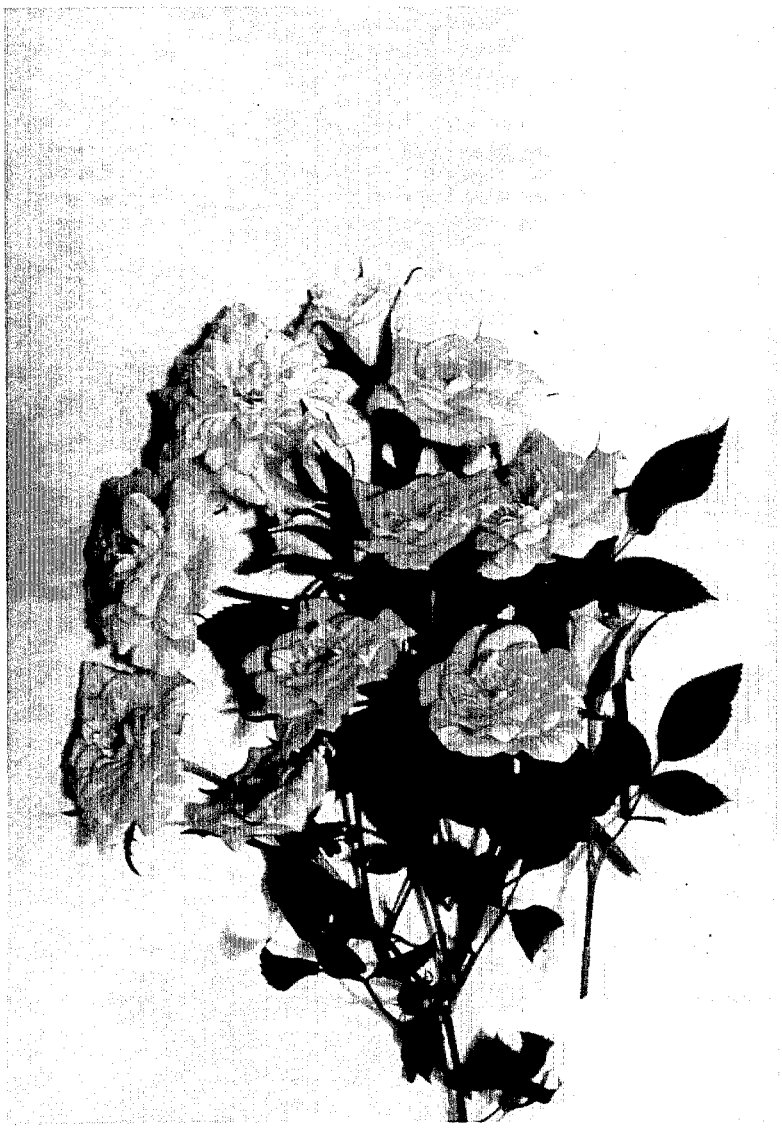

* * * * *